United States Patent [19]

Baram

[11] Patent Number: 4,981,787

[45] Date of Patent: Jan. 1, 1991

[54] METHOD FOR DIAGNOSIS OF PERIODONTAL DISEASE BY DETECTION OF L-ALANINE AMINOTRANSFERASE

[75] Inventor: Peter Baram, LaJolla, Calif.

[73] Assignee: Xytronyx, Inc., San Diego, Calif.

[21] Appl. No.: 310,789

[22] Filed: Feb. 14, 1989

[51] Int. Cl.[5] .......................... C12Q 1/52; C12Q 1/48
[52] U.S. Cl. ........................................ 435/16; 435/7;
   435/15; 435/810; 435/805; 435/30
[58] Field of Search .................. 435/15, 16, 810, 7,
   435/30

[56] References Cited

U.S. PATENT DOCUMENTS 3,691,018  9/1972  McNamara ...................... 195/103.5
4,801,535  1/1989  Babler et al. ............................ 435/16

FOREIGN PATENT DOCUMENTS 0151536  8/1985  European Pat. Off. .................. 1/52
0022698  2/1982  Japan ..................................... 435/16
0024181  2/1985  Japan ..................................... 435/16
0169766  9/1985  Japan ..................................... 435/15

OTHER PUBLICATIONS

Recommendations (1972) of the Commission on Biochemical Nomenclature on the Nomenclature and Classification of Enzymes together with their Units and the Symbols of Enzyme Kinetics, pp. 156-159.
Bang et al., Archs Oral Biol., 15:445-451 (1970).
Bang et al., Helv. Odont. Acta, 16:89 (1972).
Chambers et al., J. Periodon., 55, No. 9, 526-530 (Sep. 1984).
Crawford et al., J. Dental Research, 62:196, Abstract No. 241 (Mar. 1983).
Friedman et al., J. Peridontol., 54, pp. 347-350 (1983).
Haffajee et al., J. Clin. Perio., 10:257-265 (1983).
Kornman, J. Period. Res., 22 (1987).
Kowashi et al., Archs Oral Biol., 24, pp. 645-650 (1979).
Lamster et al., J. Periodontal., 56, 139-147 (1985).
Lamster et al., J. Clin. Periodontal., 13, 799-804 (1986).
Larmas, Archs Oral Biol., 17, pp. 1133-1141 (1972).
LeBell et al., Archs Oral Biol., 23, pp. 925-928 (1978).
Loe et al., Acta Odont. Scand., 21:533 (1963).
Lott et al., "Clinical Enzymology: A Case-Oriented Approach," Chapter 6, pp. 111-138 (1986).
Mukherjee et al., J. Dental Research, 62:196, Abstract No. 242 (Mar. 1983).
Podhradsky et al., Archs Oral Biol., 27, pp. 615-616 (1982).
Ramfjord, J. Periodontal., 30:602 (1967).
Schenkein et al., J. Periodontol., 48, pp. 772-777 (1977).
Snyder et al., J. Dent. Res., 62:196 (1983).
Weinstein et al., Archs Oral Biol., 17:375 (1972).
Binder et al., J. Periodon. Res., 22:14-19 (1987).
Christen and Metzler, Eds., Transaminases, pp. 587-625 (1985).
Dixon and Webb, Eds., Enzymes, pp. 800-801 (1979).
Kaplan and Pesce, Eds., Clinical Chemistry: Theory, Analysis and Correlation, pp. 1088-1090 (1984).
Recommendations (1972) of the Commission on Biochemical Nomenclature on the Nomenclature and Classification of Enzymes Together with Their Units and the Symbols of Enzyme Kinetics, 1972, pp. 138 and 159.
Lamster et al., "Lactate Dehydrogenase, β-glucuronidase, and Arylsulfatase Activity in Gingival Crevicular Fluid Associated with Experimental Gingivitis in Man", Journal of Clinical Periodontology, 13, pp. 139-147 (1985).

Primary Examiner—Esther L. Kepplinger
Assistant Examiner—Toni R. Scheiner
Attorney, Agent, or Firm—Marshall, O'Toole, Gerstein, Murray & Bicknell

[57] ABSTRACT

Disclosed are methods for determining the presence of periodontal disease in mammals. The methods include the steps of (1) sampling gingival crevicular fluid, (2) assaying the crevicular fluid sample by colorimetric or other means to determine levels of alanine aminotransferase present, and (3) correlating the levels of L-alanine aminotransferase present in the crevicular fluid sample with a standard which is indicative of the presence of periodontal disease.

11 Claims, No Drawings

METHOD FOR DIAGNOSIS OF PERIODONTAL DISEASE BY DETECTION OF L-ALANINE AMINOTRANSFERASE

BACKGROUND OF THE INVENTION

The present invention relates generally to methods for determining the presence of active periodontal disease in mammals through assaying gingival crevicular fluid for the presence of intracellular enzymes. Specifically, the invention relates to methods for the determination of periodontal disease through assaying crevicular fluid for the presence of elevated levels of the enzyme L-alanine aminotransferase (E.C. 2.6.1.2) (ALT).

ALT is an intracellular enzyme widely distributed among mammalian tissues. Following acute tissue injury in the course of disease, trauma or toxicity, damaged cells release ALT into the circulation, interstitial fluid, inflammatory exudate and other bodily fluids. Elevated ALT in humans is indicative of tissue injury, most often associated with diseases of the liver.

Periodontal diseases are inflammatory diseases of microbial etiology affecting the supporting tissues of the teeth. The term "periodontal disease" encompasses two major and distinct subclasses of disease, gingivitis and periodontitis. Gingivitis is characterized by inflammation of the gums without bone loss or loss of connective tissue attachment. Gingivitis is a precondition for, but does not necessarily lead to, periodontitis which is characterized by progressive formation of periodontal pockets between the gum tissue and tooth, resulting from loss of connective tissue attachment and bone loss, eventually leading to tooth loss. Presently available methods of measuring periodontal disease include subjective observational indices such as those of Loe, H. and P. Silness, *Acta Odont. Scand.*, 21:533 (1963) for gingivitis, and Ramfjord, S., *J. Periodontol.*, 30:602 (1967) for periodontitis. These indices for periodontitis are based on criteria such as bleeding on gentle probing, pocket depth, attachment loss, and radiographic evidence of bone loss. Unfortunately, these clinical indicators, with the exception of bleeding on probing, are generally acknowledged to be reflective of past disease and prior damage. Of these indicators, only bleeding on probing (bleeding of gum tissue due to probing of the gum line or pocket with a hard instrument, e.g., probe or curet) has been claimed to correlate with active periodontal disease. Nevertheless, bleeding itself is a subjective indicator of disease and the diagnostic value of bleeding on probing has been questioned, as such bleeding appears to be associated with a high proportion of false positive indications of periodontal disease. See Haffajee, A. D., S. S. Socransky and J. M. Goodson, *J. Clin. Perio.*, 10:257-265 (1983).

Other methods have been proposed for the diagnosis of periodontal disease. Because both gingivitis and periodontitis are characterized by accumulation and flow of crevicular fluid (a transudate of serum) at the gingival sulcus and pockets, measurement of the volume of crevicular fluid present at a site has been proposed as a diagnostic method for the detection of periodontal disease. An instrument known as the Periotron (Harco Electronics Ltd.; Winnipeg, Canada) makes use of this principle by galvanometrically measuring the volume of crevicular fluid absorbed by small strips of porous material known as Periopaper (Harco; Tustin, California) which are inserted into the crevicular space between the tooth and gum.

Still other methods relate to analysis of components of crevicular fluid for the diagnosis of periodontal disease. Kornman, *J. Period. Res.*, 22, (1987) discloses methods correlating the presence of collagenase in crevicular fluid with the severity of periodontal disease. A device (Periocheck, Advanced Clinical Technologies, Inc., Westwood, Mass.) is available which assays for neutral proteases to determine the presence of periodontal disease. The source of both collagenase and neutral proteases has been suggested to be polymorphonuclear leucocytes migrating into the crevice. Other components of crevicular fluid such as chondroitin-4-sulfate, the presence of which is considered indicative of bone destruction, have been found to differ in crevicular fluid associated with gingivitis and crevicular fluid associated with periodontitis. Prostaglandin $E_2$, a mediator of inflammation, has also been indicated to be associated more closely with periodontitis than with gingivitis.

The enzyme aspartate aminotransferase (AST) is an intracellular enzyme widely distributed among tissues and organs of the body. Elevated levels of AST in the blood and other bodily fluids is indicative of tissue inflammation and cellular damage. In particular, AST has been used in the detection of disorders of the liver, heart and skeletal muscles. The ratio of AST to ALT (formerly SGOT/SGPT ratio) is useful in assessing the extent of hepatic damage; the greater the ratio, the worse the damage.

It has been found that elevated levels of AST in crevicular fluid is highly correlative with the presence of active periodontal disease. (See abstracts presented at the American Association for Dental Research Meetings, Cincinnati, Ohio, March 17-20, 1983: Crawford, J. M., S. Mukherjee, D. A. Chambers and R. Cohen, Abstract No. 241; and Mukherjee, S., J. Crawford, D. A. Chambers and R. Cohen, Abstract No. 242; Chambers, D. A., J. M. Crawford, S. Mukherjee and R. Cohen, *J. Periodon.*, 55, No. 9, 526-530, Sept. 1984). The Crawford, et al. abstract discloses a study with dogs in which gingivitis and periodontitis were induced experimentally. Specifically, gingival health was established in five beagles and gingivitis was then allowed to develop for four weeks by introduction of a soft diet and withdrawal of brushing. Periodontitis was then induced by ligation of the dogs' teeth. Crevicular fluid samples were collected at weekly intervals in volumetric capillary tubes after isolation and drying of teeth. The abstract indicates that crevicular fluid obtained during the incidence of experimental periodontitis contained concentrations of AST ($3209 \pm 1435$ SFU/ml) approximately ten-fold higher at their peak than prior to ligation ($468 \pm 164$ SFU/ml) and further that crevicular fluid during the incidence of experimental gingivitis contained approximately ten-fold higher concentrations of AST than in serum ($41 \pm 4$ SFU/ml).

The Chambers, et al., *J. Periodont.* publication describes the dog study in greater detail and notes that the: average AST levels in crevicular fluid correlated neither with clinical estimations of attachment levels nor with gingival inflammation. The article did note, however, that the peak of AST activity occurring 2 weeks after ligation of teeth did coincide with the period of high levels of soft tissue destruction and osteoclast activity reported in the beagle dog model and with the period of active bone resorption in ligature-induced periodontitis in the monkey model. The article also disclosed that the level of AST in crevicular fluid did not correlate with enzyme levels in dental plaque, suggesting the absence of bacterial origin for the enzyme.

The Mukherjee Abstract describes measurement of AST levels in human crevicular fluid collected in volumetric capillary tubes from areas diagnosed as having gingivitis or periodontitis according to the periodontal disease index (PDI) of Ramfjord. Disease activity indicated by the presence or absence of bleeding upon probing was also noted. AST concentrations of crevicular fluid collected from areas showing no bleeding on probing $=0$ SFU/ml (N=4), minimal bleeding $=464\pm113$ SFU/ml (N=4) and definite bleeding $595\pm192$ SFU/ml (N=6). The analysis of data sorted according to gingivitis and periodontitis showed $363\pm182$ SFU/ml (N=4) and $424\pm119$ SFU/ml (N=3), respectively. The Abstract notes that the level of AST in crevicular fluid may correlate with the disease activity as determined by bleeding on probing.

While the references fail to demonstrate a specific positive association between elevated AST activity in gingival crevicular fluid and either attachment loss or gingival inflammation, they do indicate that there exists a general association between elevated AST levels in gingival crevicular fluid and periodontal disease activity as determined by bleeding on probing. Chambers, European patent application No. 151,536 published Aug. 14, 1985 based on U.S. patent application Ser. No. 575,552 filed Jan. 31, 1984, the disclosure of which is hereby incorporated by reference, relates to the work embodied in the article and abstracts and the recognition of the general relationship between elevated AST levels and periodontal disease activity. The application describes diagnostic methods based on the recognition that the presence of elevated levels of AST in crevicular fluid is predictive of a high probability of progressive, as opposed to non-progressive, periodontal disease and corresponding tissue damage.

According to a method described in the Chambers patent application, the crevicular fluid is collected from the gingival sulcus by means such as a microsyringe, capillary tube or absorbent strip. The volume of material is measured and the concentration of AST in the collected sample of crevicular fluid is determined by either colorimetric or immunological assay. The patent application describes a method for determining the presence of active periodontal disease in mammals comprising assaying crevicular fluid for the presence of elevated levels of aspartate aminotransferase. The application defines elevated levels as being an amount of AST substantially in excess of the level of AST normally found in the blood stream of healthy adults of the species being tested which ranges from about 4 to about 32 milli-International Units/ml (mIU/ml) depending upon the precise testing protocol used.

In addition to the work by the Chambers, et al. group on AST, the relationship between other tissue and bacterial enzymes and periodontal diseases has been studied. Lamster, et al., *J. Periodontal.*, 56, 139–147 (1985), disclose studies assessing crevicular fluid volume and activity of the enzymes lactate dehydrogenase (LDH), β-glucuronidase (BG) and arylsulfatase (AS) in crevicular fluid during the development of experimental gingivitis. Bang, et al., Helv. Odont. Acta., 16:89 (1972); Weinstein, et al., Archs. Oral Biol., 17:375 (1972) and Snyder, et al., J. Dent. Res., 62:196 (1983) relate to the presence of LDH in gingival crevicular fluid and the correlation of LDH with parameters of periodontal disease. Bang, et al., Archs. Oral Biol., 15:445–451 (1970) relate to the correlation of BG with gingival inflammation.

LDH is said to be derived primarily from cells in the sulcular epithelium, but fibroblasts and polymorphonuclear leucocytes that lyse in the crevice also contribute to the LDH pool. BG is said to be primarily derived from degradation of lysosomal granules of infiltrating polymorphonuclear leucocytes and macrophages. The pattern of AS activity was characterized as being between that of LDH and BG with sources of this enzyme including polymorphonuclear leucocytes, mast cells and fibroblasts.

Crevicular fluid "resting" volumes were determined by inserting a filter paper strip into the gingival sulcus until mild resistance was felt and leaving the strip in place for 30 seconds before removing the strip and determining the volume of fluid absorbed. After removal of the strip, the crevicular fluid "flow" volume was determined by waiting 30 seconds and inserting a second filter paper strip into the site for 3 seconds. Analysis of data collected from subjects subjected to experimental gingivitis indicated that while clinical inflammation increased during the 4 weeks of the study, the concentrations and total activity (concentration times sample volume) of BG and AS rose during the onset of gingivitis but peaked or leveled off after reaching a maximum 2 or 3 weeks into the study. The data indicated that an increase in fluid volume without a corresponding increase in BG or AS activity occurred during the latter part of the trial. The increase in LDH concentration and total activity during the experiment was not dramatic and was consistent with an earlier experiment wherein the concentration of LDH in crevicular fluid was higher in subjects with healthy gingiva than with mildly inflamed gingiva Lamster, et al. also suggested that reporting of crevicular fluid constituent data in terms of concentration alone might be inadequate and that it might be desirable to report enzyme data in terms of both concentration and total activity of the sample.

Lamster, et al., J. Clin. Periodontal., 13, 799–804 (1986), present data wherein LDH, BG and AS concentrations and total activities for 30 second samples were assayed for a group of periodontitis patients and a control group. Negative or low positive correlation coefficients were determined between enzyme concentrations and gingival index (GI) and probing depth. On the other hand, a "modest, but not absolute" correlation between increasing severity of pathology and total enzyme activity for a 30 second sample was suggested by the data. Lamster, et al. suggested, therefore, that total activity in a standardized sample might be a more appropriate means of reporting crevicular fluid constituent data.

More recently, Chambers, et al. U.S. patent application Ser. No. 262,995 filed Oct. 26, 1988, the disclosure of which is incorporated herein by reference, revealed the results of an experimental study of ligature-induced periodontitis in dogs and a longitudinal study of periodontitis patients, regarding measurement of activity of AST in gingival crevicular fluid (GCF). In the application, it was shown that the total activity of AST present in a GCF sample taken for a selected brief period of time provided a better correlation with periodontal disease activity than did assaying for the AST concentration of GCF. In addition, it was found that the total AST activity in the GCF samples was indicative of both the severity and type of periodontal disease, either gingivitis or periodontitis.

In spite of the various advances made in the art, a simple, reliable means for an enzymatic determination of the presence of periodontal disease is desired. Such a method might be used for diagnosis of such disease or for determination of the efficacy of treatment of that periodontal disease condition. The monitoring of periodontal disease is a nontrivial concern because of the serious nature of continuing or repeating treatments for periodontitis, which involve administration of drugs, root planing or surgery. Current methods such as monitoring of the clinical parameters of probing depths and radiographic interpretations of the bone provide only a belated evaluation of treatment efficacy. Accordingly, improved approaches are clearly desired.

SUMMARY OF THE INVENTION

The invention relates to methods for determining the presence of active periodontal disease in mammals. The invention also provides a method for determining the efficacy of treatment of periodontal disease conditions. Specifically, such methods comprise assaying crevicular fluid for the presence of elevated levels of the enzyme ALT. It has been found that levels of ALT present in crevicular fluid correlate with indicators of periodontal disease severity and past disease and that levels elevated over those normally found in the crevicular fluid of those having no past history or present indications of periodontal disease are indicative of the presence, severity and type of active periodontal disease.

According to methods of the invention, gingival crevicular fluid (GCF) is sampled from the interface of the gum and tooth and is assayed for the presence of ALT. According to one method, the concentration of ALT in the GCF sample is determined and is compared to a standard indicative of the presence of periodontal disease. According to a preferred embodiment of the invention, GCF is collected from a given site in the gingival sulcus for a selected brief period of time, preferably of from about one second to about 3 minutes and most preferably from about 5 to 30 seconds. GCF samples so obtained will be of varying volumes depending upon the condition of the specific sample site. The GCF so sampled, of whatever volume, is then assayed to determine, not the concentration, but the total activity of ALT present. The total activity of ALT in the sample so assayed is then correlated with a standard established for the selected period of sampling time, which standard is indicative of the presence, type or severity of periodontal disease. The improved methods of the invention are not only useful for the diagnosis of periodontal disease but are also useful for determining the efficacy of treatment of periodontal disease conditions by determining the activity of the periodontal disease condition at a gingival site subjected to such treatment.

DETAILED DESCRIPTION

According to practice of the invention, gingival crevicular fluid is sampled from the intracrevicular space between the teeth and gum tissue. The fluid sampled during that time is then assayed to determine the concentration of ALT, according to chemical or immunological methods well known to the art. The concentration of ALT determined is then correlated with a standard which is indicative of the presence of active periodontal disease. When the ALT concentration is in excess of the standard, the presence of active periodontal disease is indicated.

In a preferred embodiment of the invention, the crevicular fluid is collected from a particular site in the gingival sulcus for a selected brief period of time. The entire volume of fluid obtained during that time period is then assayed for the total activity of ALT, again using methods well known to the art. The total quantity of ALT thus determined for the sample is then compared with a standard established for the selective sampling period, which is indicative of the presence, type or severity of active periodontal disease.

Crevicular fluid may be collected from the gingival sulcus by a variety of means according to the present invention including a microsyringe with a fine (preferably blunt) needle or a capillary tube which need not be calibrated. Samples may also be obtained by means of pledgets, cotton swabs or filamentous material such as dental floss. Preferably, such fluid is sampled by means of absorbent strips of paper such as those known as Periopaper (Harco; Tustin, Calif.). The sample is collected by direct contact of the sampling means with crevicular fluid at the gingival sulcus. The sample means should be of sufficient capacity to accommodate the volume of crevicular fluid collected for a selected sampling period. It is generally desirable that this volume should be less than or equal to about 1 $\mu l$ but the sample volume could be substantially higher (i.e., from 1–10 $\mu l$) when the flow rate is greatly elevated. The fluid sampled can be less than the total capacity of the sample means. The absence of fluid or of ALT enzyme at a crevicular site is generally indicative of health and may be interpreted as such. It is not necessary that the absorbent means measure the volume of the fluid absorbed, but it is generally desired that the means absorb all of the fluid in the crevicular space.

The preferred method of the invention involves sampling of crevicular fluid according to a specific methodology whereby crevicular fluid at a given site is sampled over a selected standardized brief period, preferably of from about 5 seconds to about 3 minutes and most preferably from about 5 to 30 seconds. The sampling period must be uniform with respect to the standard selected in order to determine the presence, type or severity of periodontal disease. The oral fluid sample, obtained by whatever means, is then assayed to determine the total quantity of ALT present. Chemical or immunological methods (including the use of monoclonal antibodies specific for ALT) such as are well known in the art may be used to conduct such analysis.

For example, in Lott, et al., "Clinical Enzymology: A Case-Oriented Approach," Chapter 6, p. 132, 1986, it is noted that a well known reaction

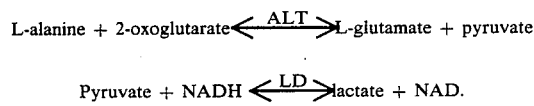

where LD is lactate dehydrogenase, and NAD is nicotime adenine dinucleotide).

As the quantity of NADH decreases, due to the second reaction, the decrease in absorbence with time is followed at 340 nm. Other reaction schemes for the determination of ALT activity would be readily apparent to those of skill in the art. Such schemes could use a wide variety of materials including diazo dyes for the determination of ALT activity. ALT is a very stable enzyme; its values do not change in 24 hours, and it is stable for at least one week at 4° C.

EXAMPLE 1

As part of an ongoing longitudinal study of periodontitis, patients enrolled in a quarterly maintenance therapy program for more than two years, ALT activity was measured in gingival crevicular fluid (GCF) samples collected from 19 of these patients. The GCF samples were collected over a period of 30 seconds, for 8 periodontal sites per subject for a total of 152 sites. The total activity of ALT in each GCF sample was measured. These sites were also evaluated clinically for evidence of severity of inflammation or past periodontitis.

The results are shown in Tables 1 and 2. In Table 1, it is shown that those sites with the most severe inflammation (Gingival Index 2 and GCF volume greater than 0.4 $\mu$l) tended to have elevated levels of ALT activity. In Table 2, it is seen that those sites with evidence of having suffered the most disease in the past (pocket depth greater than 4 mm and probing attachment level greater than 7 mm) also tended to have elevated ALT. These results demonstrate a positive association between ALT activity and indicators of disease severity or past disease.

TABLE 1

ASSOCIATION OF GCF ALT WITH CLINICAL MEASUREMENTS OF PERIODONTAL INFLAMMATION

| | Gingival Index | | | Crevicular Fluid Volume ($\mu$l) | | |
|---|---|---|---|---|---|---|
| | 0 | 1 | 2 | 0-0.2 | 0.21-0.4 | >0.4 |
| mean ALT activity for a 30 sec. sample ($\mu$IV) | 307 | 409 | 1141 | 356 | 414 | 1111 |

TABLE 2

ASSOCIATION OF GCF ALT WITH CLINICAL MEASUREMENTS OF PAST PEROIDONTAL DISEASE

| | Probing Pocket Depth (mm) | | | Probing Attachment Level (mm) | | |
|---|---|---|---|---|---|---|
| | 1-3 | 4 | >4 | 2-5 | 5-7 | >7 |
| mean ALT activity for a 30 sec. sample ($\mu$IU) | 335 | 619 | 1789 | 341 | 330 | 1196 |

Numerous modifications and variations of the above-described invention are expected to occur to those of skill in the art. In particular, it is expected that modifications of the assay procedures will be developed for colorimetric assay kits indicative of the potential presence of periodontal disease. Accordingly, only such limitations as appear in the following claims should be placed thereon.

I claim:

1. A method for determining the presence of active periodontal disease in mammals, comprising the steps of sampling gingival crevicular fluid, performing an assay on said gingival crevicular fluid for the presence of elevated levels of L-alanine aminotransferase, and correlating the level of L-alanine aminotransferase with a standard indicative of the presence of active periodontal disease.

2. The method according to claim 1 comprising assaying gingival crevicular fluid for the presence of elevated concentrations of L-alanine aminotransferase.

3. The method according to claim 1 wherein the gingival crevicular fluid is sampled for a selected brief period of time, between 1 second and 3 minutes, and the total quantity of L-alanine aminotransferase in the fluid is determined.

4. The method according to claim 3 wherein the crevicular fluid is sampled for a selected brief period of between 5 seconds and 30 seconds.

5. The method of claim 1 wherein the crevicular fluid is sampled by means of a capillary tube.

6. The method of claim 1 wherein the crevicular fluid is sampled by means of a syringe.

7. The method of claim 1 wherein the crevicular fluid is sampled by means of an absorbent strip.

8. The method of claim 1 wherein said assay is a colorimetric assay.

9. The method of claim 1 wherein said assay is an immunological assay.

10. A method for determining the efficacy of treatment of periodontal disease conditions, comprising the steps of sampling gingival crevicular fluid, assaying said gingival crevicular fluid for the presence of elevated levels of L-alanine aminotransferase and correlating the level of L-alanine aminotransferase with a standard indicative of the efficacy of treatment of the periodontal disease state.

11. A diagnostic kit for determining the presence of active periodontal disease in mammals, comprising:
a means for sampling crevicular fluid selected from the group consisting of dental floss, pledgets and cotton swabs;
a means for assaying the crevicular fluid for the concentration of L-alanine aminotransferase; and
a means for correlating the level of L-alanine aminotransferase with a standard indicative of the presence of active periodontal disease.

UNITED STATES PATENT AND TRADEMARK OFFICE
CERTIFICATE OF CORRECTION

PATENT NO. : 4,981,787

DATED : January 1, 1991

INVENTOR(S) : Baram

It is certified that error appears in the above-identified patent and that said Letters Patent is hereby corrected as shown below:

On title page;
OTHER PUBLICATIONS section, right side, "Recommendations (1972) of the Commission on Biochemical Nomenclature on the Nomenclature and Classification of Enzymes Together with Their Units and the Symbols of Enzyme Kinetics," "pp. 138" should be --pp. 158--.

Column 2, line 52, "contained!d" should be --contained--.

Column 2, line 60, delete ":" (the colon).

Column 4, line 37, after "gingiva" insert --.-- (a period).

Column 5, line 52, "cf" should be --of--.

Column 6, line 53, after "reaction "insert --scheme for determination of ALT is as follows:--.

Column 6, line 61, before "where" insert --(--.

Column 6, lines 61 and 62, "nicotime" should be --nicotine--.

Column 7, line 39, "($\mu$IV)" should be --($\mu$IU)--.

Signed and Sealed this
Nineteenth Day of January, 1993

Attest:

DOUGLAS B. COMER

*Attesting Officer*  *Acting Commissioner of Patents and Trademarks*